United States Patent
Featonby et al.

(10) Patent No.: US 10,451,569 B2
(45) Date of Patent: Oct. 22, 2019

(54) APPARATUS AND METHOD FOR SCANNING A STRUCTURE, AND COLLIMATOR THEREFOR

(71) Applicant: JOHNSON MATTHEY PUBLIC LIMITED COMPANY, London (GB)

(72) Inventors: Paul David Featonby, Northumberland (GB); Emanuele Ronchi, Cleveland (GB)

(73) Assignee: Johnson Matthey Public Limited Company, London, England (GB)

( * ) Notice: Subject to any disclaimer, the term of this patent is extended or adjusted under 35 U.S.C. 154(b) by 294 days.

(21) Appl. No.: 15/301,519

(22) PCT Filed: Mar. 31, 2015

(86) PCT No.: PCT/GB2015/051002
§ 371 (c)(1),
(2) Date: Oct. 3, 2016

(87) PCT Pub. No.: WO2015/150796
PCT Pub. Date: Oct. 8, 2015

(65) Prior Publication Data
US 2017/0122887 A1    May 4, 2017

(30) Foreign Application Priority Data
Apr. 1, 2014 (GB) .................................. 1405862.2

(51) Int. Cl.
*G01N 23/00* (2006.01)
*G01N 23/18* (2018.01)

(52) U.S. Cl.
CPC ....... *G01N 23/18* (2013.01); *G01N 2223/316* (2013.01); *G01N 2223/3303* (2013.01)

(58) Field of Classification Search
CPC ................................ A61B 6/032; A61B 6/587
See application file for complete search history.

(56) References Cited

U.S. PATENT DOCUMENTS

| 4,280,178 A | 7/1981 | Nassi et al. |
| 4,638,165 A * | 1/1987 | Glasow ............... H01L 31/1185 250/370.09 |

(Continued)

FOREIGN PATENT DOCUMENTS

| DE | 2642064 | 3/1978 |
| GB | 2496736 | 5/2013 |
| WO | 99/29233 | 6/1999 |

OTHER PUBLICATIONS

United Kingdom Combined Search and Examination Report dated Sep. 23, 2015; Application No. GB1505573.4.

(Continued)

*Primary Examiner* — Dani Fox
(74) *Attorney, Agent, or Firm* — BakerHostetler

(57) ABSTRACT

An apparatus for scanning a structure to detect density differences between different structure parts, the apparatus includes a source of gamma radiation, a plurality of first detectors arranged to detect radiation emitted by the source along a plurality of respective first paths, a plurality of second detectors arranged to detect radiation emitted by the source along a plurality of respective second paths. Each first and second path is substantially aligned with a respective radius of a circle centered on the source, and an angular separation between at least two neighboring first paths is S. The first and second detectors and the source are arranged for rotation in a fixed relationship with respect to each other, about an axis of rotation located between the source and detectors, wherein the axis of rotation is substantially orthogonal to the circle. An asymmetric collimator block directs gamma radiation from the source to the detectors.

17 Claims, 3 Drawing Sheets

(56) References Cited

U.S. PATENT DOCUMENTS

| | | | |
|---|---|---|---|
| 5,768,331 A | 6/1998 | Gordon et al. | |
| 7,852,981 B2 | 12/2010 | Luo et al. | |
| 2007/0081624 A1* | 4/2007 | Nabatame | A61B 6/032 378/19 |
| 2011/0158381 A1* | 6/2011 | Wu | A61B 6/032 378/19 |

OTHER PUBLICATIONS

United Kingdom Search Report dated Oct. 2, 2014; Application No. GB1405862.2.

International Search Report PCT/GB2015/051002 dated Sep. 2, 2015.

* cited by examiner

APPARATUS AND METHOD FOR SCANNING A STRUCTURE, AND COLLIMATOR THEREFOR

The present invention relates to an apparatus and method for scanning a structure, and a collimator therefor, and relates particularly, but not exclusively, to an apparatus, collimator and method for scanning a structure using gamma radiation to detect differences in density between different parts of the structure. The apparatus and method of the invention have particular benefits for use in an undersea pipeline inspection apparatus.

It is known to use gamma radiation for scanning structures, for example to obtain information about the density within the structure or to identify flaws such as cracks or corrosion in a structure. This is particularly useful for inspecting pipes subsea, where it is not always possible to inspect the pipe from the interior. Gamma scanning is also used for obtaining information about other industrial structures such as distillation columns and the like.

An apparatus for scanning structures such as a pipeline or process vessel using gamma radiation is described in GB 2496736 A. This apparatus comprises a source of gamma radiation and an array of detectors. The apparatus is capable of being arranged with the structure to be scanned, such as a pipeline, positioned between the source and detectors so that radiation emitted by the source can pass along a plurality of paths through a portion of the structure to the detectors. The number of detectors in the array may range from fewer than 10 up to more than 100, e.g. up to 150, depending on the application.

A typical detector for detecting gamma radiation comprises a scintillating crystal. Gamma rays entering the scintillation crystal interact with the scintillating material to produce photons in the visible and/or ultraviolet region. These scintillation photons are detected using a photodetector, for example a photomultiplier tube, which outputs an electrical pulse providing information about the number and energy of the incident gamma photons. Counting the number gamma photons transmitted from the source to the detectors, through the structure being scanned, enables differences in the density of different parts of the structure to be detected.

To obtain high resolution data, a large number of detectors are used, closely spaced from one another. The detectors are arranged in an arc centred on the structure to be scanned. In operation, the source and array of detectors are arranged in fixed relationship with respect to each other, and are rotated around the structure to be scanned. In this way, information about the density of the structure along a plurality of paths is obtained, enabling a high resolution density map of the structure to be calculated. The apparatus may also be translated axially to scan different sections of the structure. This technique has similarities with medical imaging techniques such as x-ray tomography.

The resolution of the tomography image obtained is related to the number of detectors used, which in turn determines the number of radiation paths between the source and a detector that pass through the structure to be imaged.

In practice, the number of detectors is limited due to space constraints. Firstly, in order to detect to the gamma radiation that has passed through the structure it is necessary to use detectors of sufficient size and density to stop the gamma photons so that they do not pass through the detector undetected. Secondly, in order to maintain a high resolution, typically the radiation travelling towards each detector must be collimated sufficiently to significantly reduce detection of gamma photons which have been scattered from a path other than the direct path from the source to a particular detector. The detection of scattered photons is typically further reduced by providing shielding material around the detectors so that the non-detecting surfaces of the detector, except for the portion of the collecting surface in optical communication with the photodetector, are protected from radiation.

In subsea applications, additional space constraints arise. When operating at a depth of 1000 meters under water, the pressure is 100 atmospheres and increases by a further 100 atmospheres for each additional 1000 meters of depth. The apparatus must be able to withstand this pressure yet remain sufficiently compact for deployment using remotely operated vehicles capable of operating at the required depth.

It is therefore difficult to improve resolution by reducing the size of the detectors and associated collimators or the spacing between neighbouring detectors to enable detection of radiation along further paths through the structure being scanned.

Even if were possible to reduce the size of the detectors and collimators, this would lead to a reduction in the count rate detected at each detector. The consequent reduction in signal to noise ratio would reduce resolution and increase the scan time required.

Additionally, the presence of even small calibration errors in some or all of the detectors means that increasing the number of detectors does not necessarily improve the resolution of the image obtained.

Preferred embodiments of the present invention seek to overcome one or more of the above disadvantages of the prior art.

According to a first aspect of the invention there is provided an apparatus for scanning a structure to detect differences in density between different parts of the structure, the apparatus comprising:

a source of radiation;

a plurality of first detectors arranged to detect radiation emitted by said source along a plurality of respective first paths; and a plurality of second detectors arranged to detect radiation emitted by said source along a plurality of respective second paths;

wherein each said first and second path is substantially aligned with a respective radius of a circle centred on the source;

wherein an angular separation between at least two neighbouring first paths is S;

wherein the first and second detectors and the source are arranged for rotation in a fixed relationship with respect to each other, about an axis of rotation located between the source and the detectors, wherein said axis of rotation is substantially orthogonal to said circle;

wherein at least one said first path is located on a first side of a plane containing the source and said axis of rotation, at an angle of $A+n \cdot S$ to said plane, where A is an arbitrary offset angle and n is an integer; and wherein at least one said second path is located on a second side of said plane, at an angle of $A+(n+f) \cdot S$ to said plane, where $0<f<1$.

By offsetting the position of at least one second detector relative to that of the first detectors by a fraction of the first detector spacing S, the number of radiation paths along which density information is obtained is effectively increased.

In contrast, when a symmetric array of detectors (i.e. an array of detectors which is symmetric about a line drawn from the source through the axis of rotation) is rotated through 360° about a structure, the detectors in the left-hand half of the array effectively provide the same information as those in the right-hand half of the array. This can be understood by considering that a radiation path from the source to a selected detector in the left-hand half of the array, when the source and detectors are in an initial position, coincides with a path from the source to a detector in the right-hand half of the array when the source and detectors are rotated so that the source moves to the initial position of the selected detector. Thus the information obtained by each detector in the left-hand half of the array is replicated by a corresponding detector in the right-hand half of the array. This is illustrated by FIG. 1, which shows a radiation source 120 and two arrays of detectors 130, 140, each comprising a pair of detectors 130$a$, 130$b$ and 140$a$, 140$b$, rotatable in a fixed relationship with respect to each other about an axis of rotation 160. The detectors 130$a$, 130$b$ and 140$a$, 140$b$ are arranged symmetrically about a plane 170 passing through the source 120 and the axis of rotation 160. Respective paths 132$a$, 132$b$, 142$a$, and 142$b$ from the source 120 to the detectors 130$a$, 130$b$, 140$a$ and 140$b$ are indicated. The angular spacing of the pair of paths 132$a$, 132$b$ is labelled as S. The paths 142$a$, 142$b$ to the right-hand array of detectors 140$a$, 140$b$, are aligned with the mirror-image positions of the paths 132$a$, 132$b$ to the left-hand array of detectors 130$a$, 130$b$ as reflected by the plane 170. When the apparatus is rotated from its initial position (FIG. 1A) such that the source 120 coincides with the initial position X of the left-hand detector 130$a$ (FIG. 1B), the path 142$a'$ from the source 120 to the right-hand detector 140$a$ (FIG. 1B) coincides with the initial path 132$a$ from the source 120 to the left-hand detector 130$a$ (FIG. 1A). Similarly, when the apparatus is rotated further such that the source 120 coincides with the initial position Y of the right-hand detector 140$a$ (FIG. 10), the path 132$a''$ from the source 120 to the left-hand detector 130$a$ (FIG. 1C) coincides with the initial path 142$a$ from the source 120 to the right-hand detector 140$a$ (FIG. 1A). Thus the information obtained by the left-hand detector 130$a$ is effectively duplicated by the corresponding right-hand detector 140$a$. Similarly, it can be shown that the information obtained by the left-hand detector 130$b$ is effectively duplicated by the corresponding right-hand detector 140$b$.

In some applications, the two-fold redundancy provided by a symmetric array of detectors may be useful in that it can be used to reduce scan times or to compensate for hardware failures in some of the detectors.

However, in the present invention, one side of the array is instead offset by a fraction of the detector spacing S, i.e. by f·S where 0<f<1, relative to the symmetric arrangement, to provide additional detection paths through the structure being scanned during a single 360° scan. The detection paths corresponding to the plurality of second detectors are not aligned with the mirror-images of the detection paths corresponding to the plurality of first detectors and therefore no longer provide the same information during a 360° scan. Instead, the detection paths corresponding to the plurality of second detectors are equivalent to paths interposed between the detection paths corresponding to the plurality of first detectors, when considered over a 360° rotation of the detectors and source. In this way, the effective spacing between the paths through the structure along which radiation is detected is reduced, improving the resolution of the images obtained.

The additional information provided by the plurality of second detectors could alternatively be achieved by shifting all the detectors to a new position, rotated by a fraction of a detector spacing S relative to the source, and performing a second scan at this new position. However, this would require additional moving parts and would require extra time to shift the detectors and perform the additional scan. The present invention provides the advantage that the additional information is obtained with the detectors in one position relative to the source, and in a single scan, thereby simplifying the apparatus, thereby reducing calibration errors, and reducing scan time.

Advantageously, the present invention improves resolution without reducing the size of the detectors, since the first and second pluralities of detectors may be located in non-overlapping positions. Therefore there is no reduction in count rate at each detector and the scanning time does not have to be significantly increased.

In one embodiment, f is substantially equal to 0.5.

This arrangement effectively halves the detector spacing relative to a symmetric arrangement of detectors about the source.

In one embodiment, an angular separation between at least two neighbouring second detectors is S.

Preferably, the apparatus comprises substantially equal numbers of first and second detectors.

In one embodiment, said first paths are located on said first side of said plane, at respective angles from said plane of A+n·S, where n=0, 1, 2, . . . ; and said second paths are located on said second side of said plane, at respective angles from said plane of A+(n+f)·S, where n=0, 1, 2, . . . .

Preferably, the first and second detectors are arranged for rotation by 360° about said axis of rotation.

The first and second paths may be defined, at least in part, by respective collimator channels.

The first and second paths may be defined, at least in part, by respective detection surfaces of said detectors.

The apparatus may further comprise at least one collimator block, comprising: a plurality of first collimator channels, wherein said first paths are defined at least in part by respective first collimator channels; and/or a plurality of second collimator channels wherein said second paths are defined at least in part by respective second collimator channels.

The source may be a gamma radiation source.

At least one said first or second detector may comprise a scintillating material for emitting light in response to incident radiation.

According to a second aspect of the invention, there is provided a collimator arrangement for an apparatus for scanning a structure to detect differences in density between different parts of the structure, the collimator arrangement comprising:

a plurality of first collimator channels defining, at least in part, a plurality of respective first radiation paths; and a plurality of second collimator channels defining, at least in part, a plurality of respective second radiation paths;

wherein each said first and second radiation path is substantially aligned with a respective radius of a circle;

wherein an angular separation between neighbouring first paths is S;

and an angular separation between at least one said first path and at least one said second path is (n+f)S, where n is an integer and 0<f<1.

The first and second collimator channels may be provided in a single block of collimating material.

According to a third aspect of the invention, there is provided a method for scanning a structure to detect differences in density between different parts of the structure, the method comprising:

providing at least one source of radiation;

providing a plurality of first detectors arranged to detect radiation emitted by said source along a plurality of respective first paths; and providing a plurality of second detectors arranged to detect radiation emitted by said source along a plurality of respective second paths;

wherein each said first and second path is substantially aligned with a respective radius of a circle having the source at its origin;

wherein an angular separation between at least two neighbouring first paths is S;

the method further comprising:

rotating said first and second detectors and said source in a fixed relationship to each other about an axis of rotation located between said detectors and the source, wherein said axis of rotation is substantially orthogonal to said circle;

wherein at least one said first path is located on a first side of a plane containing the source and said axis of rotation, at an angle of $A+n \cdot S$ to said plane, where A is an arbitrary offset angle and n is an integer; and wherein at least one said second path is located on a second side of said plane, at an angle of $A+(n+f) \cdot S$ to said plane, where $0 < f < 1$.

The method may further comprise rotating said first and second detectors and said source in a fixed relationship to each other by at least 360 degrees about said axis of rotation.

A preferred embodiment of the present invention will now be described, by way of example, and not in any limitative sense, with reference to the accompanying drawings, in which.

Figure 1:
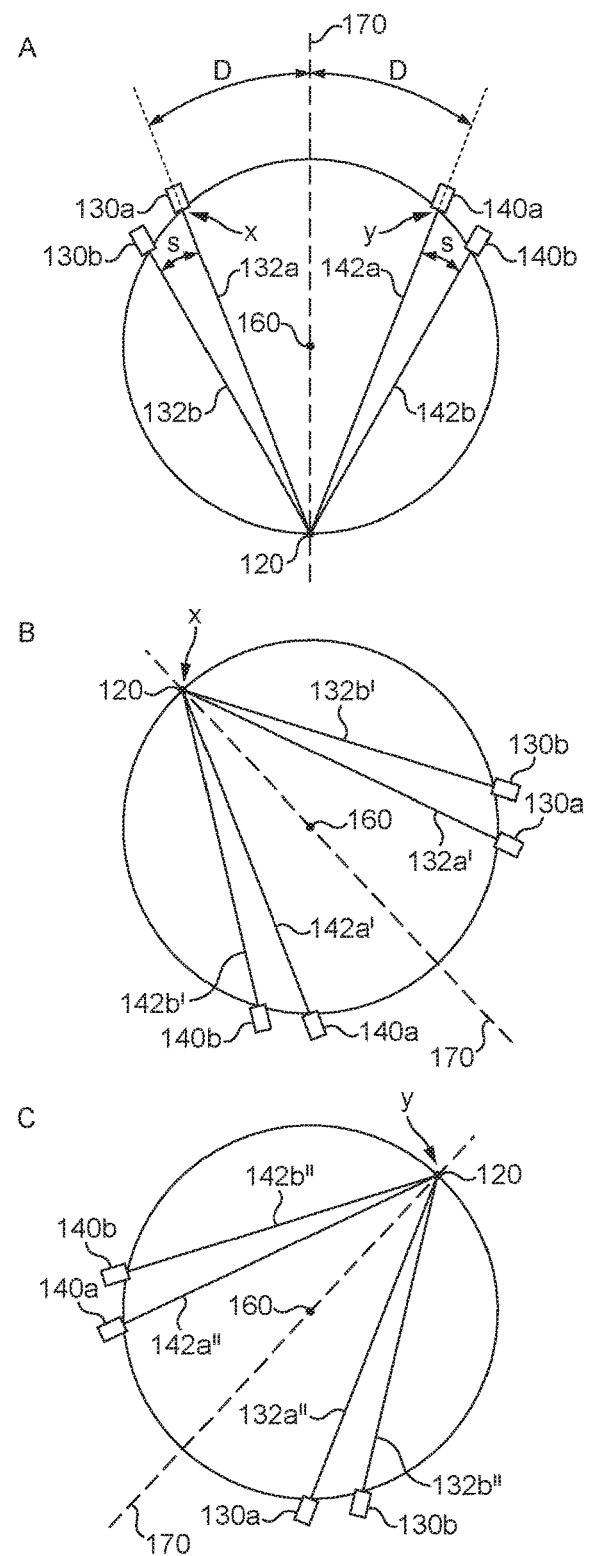
FIG. 1 illustrates a symmetric arrangement of detectors, useful for understanding the present invention.
Figure 2:
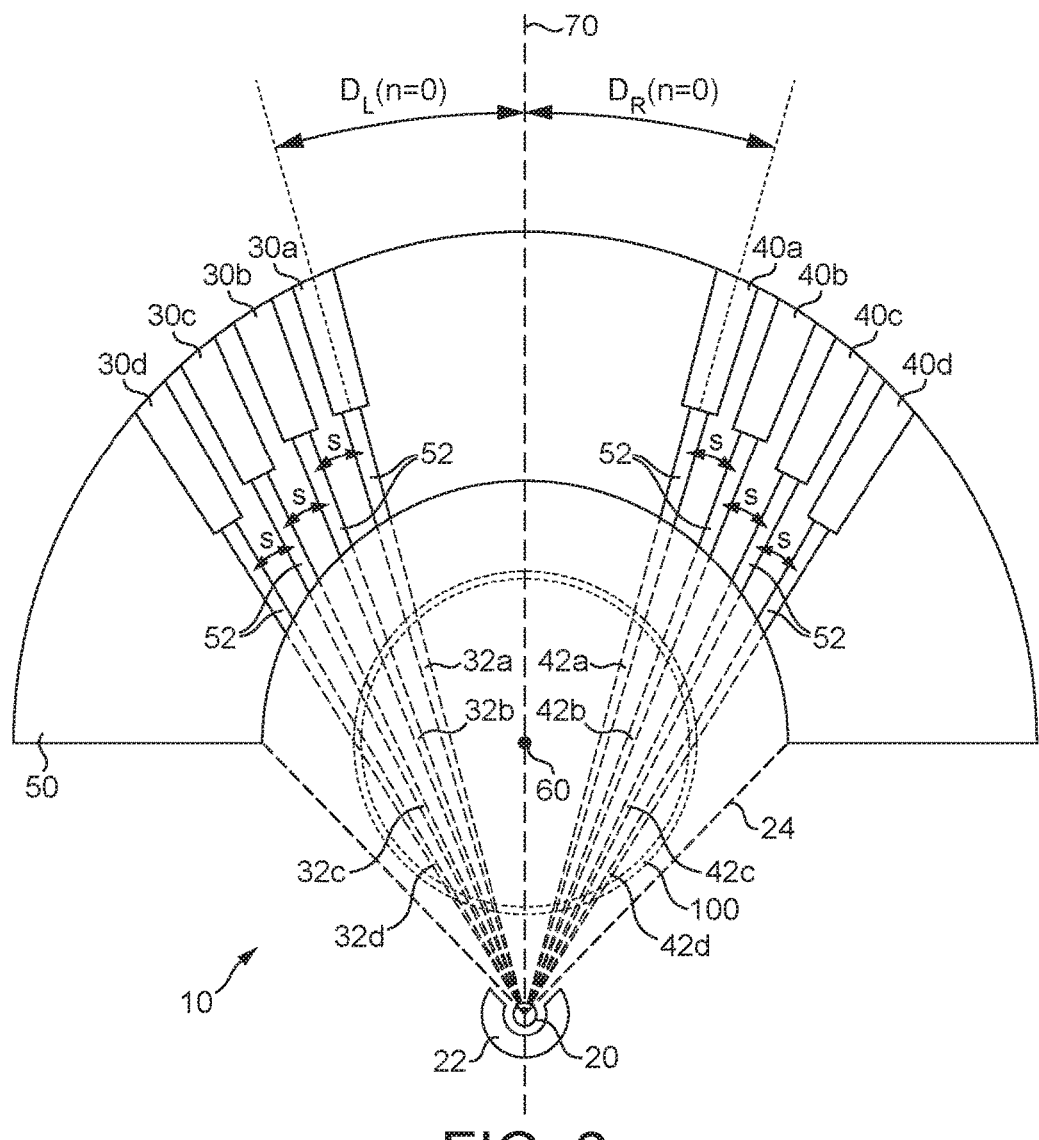
FIG. 2 is a schematic representation of a first embodiment of the present invention.

With reference to FIG. 2, an apparatus 10 according to a first embodiment of the invention will now be described. The apparatus 10 comprises a source of radiation 20, a plurality of first detectors 30a, 30b, 30c, 30d arranged to detect radiation emitted by the source 20 along a plurality of respective first paths 32a, 32b, 32c, 32d, and a plurality of second detectors 40a, 40b, 40c, 40d, arranged to detect radiation emitted by said source 20 along a plurality of respective second paths 42a, 42b, 42c, 42d. Each of the first and second paths 32, 42 is substantially aligned with or centred on a respective radius of a circle centred on the source 20.

In this embodiment, the radiation source 20 is a gamma radiation source, such as $^{137}Cs$ which has a characteristic emission at 661.7 keV, with sufficient penetrating power for scanning dense structures such as subsea pipelines. The source 20 is surrounded by a source collimator 22 having a slot for collimating radiation from the source 20 in a fan shaped beam 24 towards the detectors 30, 40. The source collimator 22 is preferably formed of a material which is highly attenuating to the radiation emitted by the source, for example a heavy alloy material. Although the present embodiment is based on gamma photon detection, it will be appreciated that the present invention can be applied to other types of radiation (e.g. neutrons).

The detectors 30a-d and 40a-d comprise a scintillating material or crystal suitable for detecting gamma photons at this source energy, for example BGO (bismuth germanate). Photodetectors (not shown) are provided for receiving light emitted by each respective scintillation crystal of the detectors 30a-d and 40a-d and outputting an electrical signal in response to the light received from the scintillating material. Processing and analysis of the electrical signals output by the photodetectors is performed to obtain an image of the structure 100 being scanned.

The skilled person will appreciate that other combinations of sources and detectors may be used as is known in the art.

A collimator block 50 is provided for collimating the radiation travelling towards each detector 30a-d, 40a-d in order to reduce the detection of gamma photons which have been scattered from a path other than the respective direct path 32a-d, 42a-d from the source to the detector 30a-d, 40a-d. The collimator block 50 is formed of a shielding material which is attenuating to gamma radiation. A dense shielding material such as lead, tungsten, or a heavy alloy may be used, which is highly attenuating to gamma radiation. Alternatively, a less dense material such as steel may be used. This provides less shielding but is not as heavy as the denser shielding materials.

The collimator block 50 includes a plurality of collimator channels 52 within it. The length of each channel 52 is determined by the requirements of the detectors 30, 40, the energy of radiation emitted by the source 20, and the shielding material used. The collimator channels 52 may be any convenient shape, although it is preferred that the cross-sections of the channels 52 have the same shape and orientation as the detecting surfaces of the respective detectors 30, 40. Preferably the walls of the channels 52 indicated in FIG. 2 are each aligned with a different radius of a circle centred on the source 20, and the ends of the channels 52 are preferably aligned to face directly towards the source 20.

The collimator block 50 also includes recesses for receiving the detectors 30, 40, which fixes the relative positions of the detectors 30, 40 and collimator channels 52. The detecting surfaces of the detectors 30, 40 are accessible to radiation passing through the respective collimator channel 52. A portion of the detecting surface of each detector 30, 40 may be covered by shielding material of the collimator block 50, for the purposes of delimiting the area of the detecting surface or for mechanically retaining the detector 30, 40 within the collimator block 50. The non-detecting surfaces of the detectors 30, 40 are shielded from incident radiation by the shielding material of the collimator blocks 50. It has been found that, even when highly dense alloys are used for shielding the detectors, a practical limitation on detector spacing is approximately 1 degree of arc.

In the present embodiment, the collimator channels 52 and recesses for holding the first and second detectors 30, 40 are all provided in a single collimator block 50, thereby reducing positioning errors. Alternatively, two or more separate collimator blocks may be provided and/or the detectors may be housed separately from the collimator channels. The detectors 34, 40, collimators 50 and associated electronics may be sealed for deployment subsea by a housing (not shown).

FIG. 2 also indicates the position of a structure 100 to be scanned by the apparatus 10, in this case a pipe 100. In operation, the structure 100 to be scanned is received between the source 20 and the detectors 30, 40 so that at least some of the paths 32, 42 between the source 20 and detectors 30, 40 pass through the structure 100.

In operation, the first and second detectors 30a-d, 40a-d and the source 20 are rotated in a fixed relationship with respect to each other, about an axis of rotation 60 located between the source 20 and the detectors 30, 40. The axis of rotation 60 is orthogonal to a plane passing through the source 20 and paths 32, 42. The axis of rotation 60 is arranged to be substantially centred on the structure 100 to be scanned.

For an apparatus for scanning a cylindrical structure such as a pipeline 100, it is preferred that the detectors 30, 40 are arranged approximately in an arc having an origin which is not the source 20, but which is centred on the pipe 100. This is illustrated by FIG. 2, which shows the detectors 30, 40 positioned substantially around an arc centred on the axis of rotation 60 which coincides with the centre of the pipe 100. This is convenient for rotation of the detectors 30, 40 and the source 20 around the pipe structure 100. However, since the collimator channels 52 are all directed towards the source 20 and not towards the axis of rotation 60, this means that most of the collimator channels 52 are not perpendicular to a tangent to that arc.

By using multiple detectors 30, 40, different paths through the structure 100 may be scanned simultaneously. Each detector 30, 40 and associated collimator channel 52 defines a different path through the structure 100 so that the number of paths which may be scanned simultaneously is equal to the number of detectors 30, 40.

The shape of the paths 32a-d, 42a-d of radiation detected at each detector 30a-d, 40a-d are defined by the detection area of the respective detector 30a-d, 40a-d (i.e. the area of the detector exposed to radiation from the source 20) and/or the collimator channels 52. Each path may correspond to a volume extending between the source and a detection area of a respective detector. In this embodiment, each of the paths has the shape of a frustum, having the source 20 at its apex and the detecting surface of a respective detector 30, 40 at its base. Each path is centred on a different radius of a circle centred on the source 20.

In FIG. 2, only eight detectors 30, 40 are shown for simplicity. However, in practice the number of detectors may vary from fewer than 10 to more than 80, e.g. up to 150, depending on the application for which the scanning method is to be used. In one embodiment, 95 detectors are used, with one detector being located on the centre line, i.e. for detecting radiation passing through the axis of rotation 60 of the apparatus. Ideally, the number of first detectors 30 and the number of second detectors 40 is substantially equal, for example being either equal or differing by one.

As illustrated in FIG. 2, the plurality of first detectors 30a-d is located on the left-hand side of a plane 70 comprising the source 20 and the axis of rotation 50. The plurality of second detectors 40a-d is located on the right-hand side of the plane 70. The first detectors 30a-d are equally spaced, indicated by an angular separation S in FIG. 2. The second detectors 40a-d are also equally spaced, with the same angular separation S. As discussed above, each path corresponds to a volume, and thus the spacing S between detection paths 32a-d, 42a-d is defined as the spacing between the centres of neighbouring detection paths.

However, the plurality of first detectors 30a-d and the plurality of second detectors 40a-s are offset by different angles with respect to the plane 70, such that the paths 32a-d and the paths 40a-d are not located at mirror image positions of each other, when reflected in the plane 70 which passes through the source 20 and axis of rotation 60. This asymmetric arrangement avoids the two-fold redundancy associated with a symmetric arrangement when scanning over a full 360 degree rotation of the apparatus, and provides additional information about the structure 100 being scanned. Due to the loss of redundancy associated with a symmetric arrangement, it may be necessary to increase the scan time in order to obtain a comparable count rate.

In the present invention, the angular offset $D_L(n)$ between the centre plane 70 and the respective first detection paths 32a-d, indicated for the innermost first path 32a (n=0) in FIG. 2, can be expressed as $D_L=A+nS$, where A is an arbitrary offset, n=0, 1, 2, . . . , $N_L-1$, with $N_L$ being the number of first detector 30a-d, and S is the detector spacing. The angular offset $D_R(n)$ between the centre plane 70 and the respective second detection paths 42a-d, indicated for the innermost second path 42a (n=0) in FIG. 2, can be expressed as $D_L=A+nS+fS$ where n=0, 1, 2, . . . , $N_R$, with $N_R$ being the number of second detectors 40a-d, and 0<f<1. As a result, the plurality of second detectors no longer records the same information as the plurality of first detectors.

In one embodiment, the detectors 30, 40 and collimator channels 52 are arranged such that f=0.5, i.e. so that the second paths 42a-d are offset by half the detector spacing S relative to the first pats 32a-d as reflected in the centre plane 70. The information recorded by the second detectors 40a-d during a full 360° rotation of the apparatus about axis 60, corresponds to that which would be recorded by similar detectors located midway between each pair of adjacent first detectors 30a-d. This arrangement therefore effectively doubles the resolution of the apparatus 10 by halving the effective spacing S between detection paths of radiation through the structure 100. With f=0.5, the pluralities of first and second detectors 30, 40 are effectively equivalent to a single array of detectors, located at the position of the first plurality of detectors 30, but comprising the same total number of detectors as the first and second pluralities of detectors and having half the detector spacing.

Figure 3:
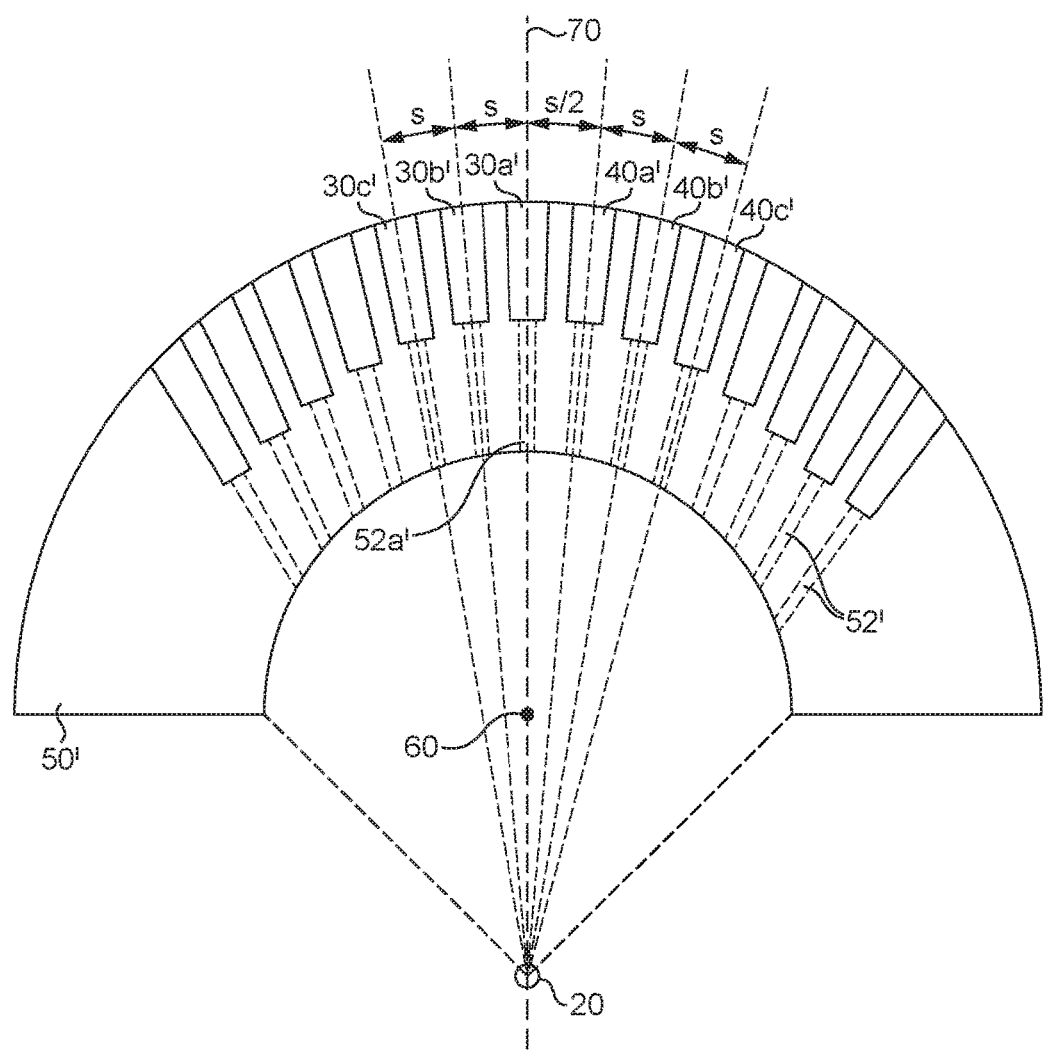
FIG. 3 is a schematic representation of a second embodiment of the present invention.

In practice, a larger number of detectors 30, 40 and corresponding collimator channels 52 would be provided than that shown in FIG. 2. For example, in one embodiment, 95 detectors are arranged to fill substantially the entire arc of the collimator block 60 between the limits of the fan shaped beam 24, with a detector spacing S of between 1 and 2 degrees of arc. In another arrangement of 2N+1 detectors, shown in FIG. 3, one of the first detectors 30a' and corresponding collimator channel 52a' is positioned at the centre line 70 (offset $D_L=0$), such that the positions of the first detectors 30' are given by $D_L=nS$ where n=0, 1, 2, . . . N, and the positions of the second detectors 40' are given by $D_R=(n+f)S$, where n=0, 1, 2, . . . N−1. That is, the arbitrary offset A may be set to zero. This means that the spacing between the adjacent first and second detectors 30a' and 40a' at the centre of the collimator block 50 is only fS, for example 0.5 S.

However, a larger separation (i.e. a larger arbitrary offset A) may be provided between the innermost first detector 30a and the innermost second detector 40a, as shown in FIG. 2, particularly for applications such as scanning the walls of a pipe 100 where information about the central region of the pipe (i.e. its content) is not required.

A relative offset of half the detector spacing between the plurality of first detectors 30 and the plurality of second detectors 40 (i.e. f=0.5) is particularly useful as it halves the effective detector spacing. However, other relative offsets may be used, such that 0<f<1.

The positions of the first and second detectors 30, 40 relative to each other and/or relative to the source 20 may be fixed. However, in some embodiments it may be possible to adjust the position of the first and/or second detectors 30, 40, and associated collimator channels 52, by a fraction of the detector spacing S relative to the source 20, thereby adjusting the value of A and/or f. In such an apparatus, scans could be combined to further reduce the effective spacing between detectors.

In a further alternative embodiment, the pluralities or first and second detectors may be subdivided into sub-pluralities having different detector spacings. This may be useful where different resolutions are desired for different parts of the structure. For example, for scanning a structure such as a pipeline 100, a lower resolution may be sufficient for the central area compared to the lateral areas if the walls of the pipeline are of greater interest than the contents of the pipeline.

It will be appreciated by persons skilled in the art that the above embodiments have been described by way of example only, and not in any limitative sense, and that various alterations and modifications are possible without departure from the scope of the invention as defined by the appended claims.

Further aspects of the invention may be as set out in the following numbered clauses:

1. An apparatus for scanning a structure to detect differences in density between different parts of the structure, the apparatus comprising:
    a source of radiation;
    a plurality of first detectors arranged to detect radiation emitted by said source along a plurality of respective first paths; and
    a plurality of second detectors arranged to detect radiation emitted by said source along a plurality of respective second paths;
    wherein each said first and second path is substantially aligned with a respective radius of a circle centred on the source;
    wherein an angular separation between at least two neighbouring first paths is S;
    wherein the first and second detectors and the source are arranged for rotation in a fixed relationship with respect to each other, about an axis of rotation located between the source and the detectors, wherein said axis of rotation is substantially orthogonal to said circle;
    wherein at least one said first path is located on a first side of a plane containing the source and said axis of rotation, at an angle of $A+n \cdot S$ to said plane, where A is an arbitrary offset angle and n is an integer; and
    wherein at least one said second path is located on a second side of said plane, at an angle of $A+(n+f) \cdot S$ to said plane, where $0<f<1$.

2. An apparatus according to clause 1, wherein f is substantially equal to 0.5.

3. An apparatus according to clause 1 or clause 2, wherein an angular separation between at least two neighbouring second paths is S.

4. An apparatus according to any of clauses 1 to 3, wherein said apparatus comprises substantially equal numbers of first and second detectors.

5. An apparatus according to any of clauses 1 to 4, wherein:
    said first paths are located on said first side of said plane, at respective angles from said plane of $A+n \cdot S$, where $n=0, 1, 2, \ldots$; and
    said second paths are located on said second side of said plane, at respective angles from said plane of $A+(n+f) \cdot S$, where $n=0, 1, 2, \ldots$.

6. An apparatus according to any of the preceding clauses, wherein said first and second detectors are arranged for rotation by 360 degrees about said axis of rotation.

7. An apparatus according to any of the preceding clauses, wherein said first and second paths are defined, at least in part, by respective collimator channels.

8. An apparatus according to any of the preceding clauses, wherein said first and second paths are defined, at least in part, by respective detection surfaces of said detectors.

9. An apparatus according to any of the preceding clauses, further comprising at least one collimator block, comprising: a plurality of first collimator channels, wherein said first paths are defined at least in part by respective first collimator channels; and/or a plurality of second collimator channels wherein said second paths are defined at least in part by respective second collimator channels.

10. An apparatus according to any of the preceding clauses, wherein said source is a gamma radiation source.

11. An apparatus according to any of the preceding clauses, wherein at least one said first or second detector comprises a scintillating material for emitting light in response to incident radiation.

12. A collimator arrangement for an apparatus for scanning a structure to detect differences in density between different parts of the structure, the collimator arrangement comprising:
    a plurality of first collimator channels defining, at least in part, a plurality of respective first radiation paths; and
    a plurality of second collimator channels defining, at least in part, a plurality of respective second radiation paths;
    wherein each said first and second radiation path is substantially aligned with a respective radius of a circle;
    wherein an angular separation between neighbouring first paths is S;
    and an angular separation between at least one said first path and at least one said second path is $(n+f)S$, where n is an integer and $0<f<1$.

13. A collimator arrangement according to clause 12, wherein said first and second collimator channels are provided in a single block of collimating material.

14. A method for scanning a structure to detect differences in density between different parts of the structure, comprising:
    providing at least one source of radiation;
    providing a plurality of first detectors arranged to detect radiation emitted by said source along a plurality of respective first paths; and
    providing a plurality of second detectors arranged to detect radiation emitted by said source along a plurality of respective second paths;
    wherein each said first and second path is substantially aligned with a respective radius of a circle having the source at its origin;
    wherein an angular separation between at least two neighbouring first paths is S;
    the method further comprising:
    rotating said first and second detectors and said source in a fixed relationship to each other about an axis of rotation located between said detectors and the source, wherein said axis of rotation is substantially orthogonal to said circle;
    wherein at least one said first path is located on a first side of a plane containing the source and said axis of rotation, at an angle of $A+n \cdot S$ to said plane, where A is an arbitrary offset angle and n is an integer; and
    wherein at least one said second path is located on a second side of said plane, at an angle of $A+(n+f) \cdot S$ to said plane, where $0<f<1$.

15. An apparatus according to clause 14, further comprising:
rotating said first and second detectors and said source in a fixed relationship to each other by at least 360 degrees about said axis of rotation.

The invention claimed is:

1. An apparatus for scanning a structure to detect differences in density between different parts of the structure, the apparatus comprising:
a source of radiation;
a plurality of first detectors arranged to detect radiation emitted by said source along a plurality of respective first paths; and
a plurality of second detectors arranged to detect radiation emitted by said source along a plurality of respective second paths;
wherein each said first and second paths is substantially aligned with a respective radius of a circle centred on the source;
wherein an angular separation between at least two neighbouring first paths is S;
wherein the first and second detectors and the source are arranged for rotation in a fixed relationship with respect to each other, about an axis of rotation located between the source and the detectors, wherein said axis of rotation is substantially orthogonal to said circle;
wherein there are 2N+1 detectors;
wherein said first paths are located on a first side of a plane containing the source and said axis of rotation and the positions $D_L$ of the first detectors are given by $D_L=nS$, where n=0, 1, 2, ... N; and
wherein said second paths are located on a second side of said plane and the positions DR of the second detectors are given by $D_R=(n+f)S$, where n=0, 1, 2, ... N−1 and where 0<f<1.

2. The apparatus according to claim 1, wherein f is substantially equal to 0.5.

3. The apparatus according to claim 1, wherein said first and second detectors are arranged for rotation by 360 degrees about said axis of rotation.

4. The apparatus according to claim 1, wherein said first and second paths are defined, at least in part, by respective collimator channels.

5. The apparatus according to claim 1, wherein said first and second paths are defined, at least in part, by respective detection surfaces of said detectors.

6. The apparatus according to claim 1, further comprising at least one collimator block, comprising: a plurality of first collimator channels, wherein said first paths are defined at least in part by respective first collimator channels; and/or a plurality of second collimator channels wherein said second paths are defined at least in part by respective second collimator channels.

7. The apparatus according to claim 1, wherein said source is a gamma radiation source.

8. The apparatus according to claim 1, wherein at least one said first or second detector comprises a scintillating material for emitting light in response to incident radiation.

9. A collimator arrangement for an apparatus for scanning a structure to detect differences in density between different parts of the structure, the collimator arrangement comprising:
a plurality of first collimator channels defining, at least in part, a plurality of respective first radiation paths; and
a plurality of second collimator channels defining, at least in part, a plurality of respective second radiation paths;
wherein each said first and second radiation path is substantially aligned with a respective radius of a circle;
wherein an angular separation between neighbouring first paths is S;
wherein there are 2N+1 collimator channels;
wherein said first paths are located on a first side of a plane containing the source and said axis of rotation and the positions $D_L$ of the first collimator channels are given by $D_L=nS$, where n=0, 1, 2, ... N; and
wherein said second paths are located on a second side of said plane and the positions $D_R$ of the second collimator channels are given by $D_R=(n+f)S$, where n=0, 1, 2, ... N−1 and where 0<f<1.

10. The collimator arrangement according to claim 9, wherein f is substantially equal to 0.5.

11. The collimator arrangement according to claim 9, wherein said first and second collimator channels are provided in a single block of collimating material.

12. A method for scanning a structure to detect differences in density between different parts of the structure, comprising:
providing at least one source of radiation;
providing a plurality of first detectors arranged to detect radiation emitted by said source along a plurality of respective first paths; and
providing a plurality of second detectors arranged to detect radiation emitted by said source along a plurality of respective second paths;
wherein each said first and second path is substantially aligned with a respective radius of a circle having the source at its origin;
wherein an angular separation between at least two neighbouring first paths is S;
the method further comprising:
rotating said first and second detectors and said source in a fixed relationship to each other about an axis of rotation located between said detectors and the source, wherein said axis of rotation is substantially orthogonal to said circle;
wherein there are 2N+1 detectors;
wherein said first paths are located on a first side of a plane containing the source and said axis of rotation and the positions $D_L$ of the first detectors are given by $D_L=nS$, where n=0, 1, 2, ... N; and
wherein said second paths are located on a second side of said plane and the positions $D_R$ of the second detectors are given by $D_R=(n+f)S$, where n=0, 1, 2, ... N−1 and where 0<f<1.

13. The method according to claim 12, wherein f is substantially equal to 0.5.

14. The method according to claim 12, further comprising:
rotating said first and second detectors and said source in a fixed relationship to each other by at least 360 degrees about said axis of rotation.

15. The apparatus according to claim 2, wherein said first and second detectors are arranged for rotation by 360 degrees about said axis of rotation.

16. The collimator arrangement according to claim 10, wherein said first and second collimator channels are provided in a single block of collimating material.

17. The method for detecting radiation according to claim 13, further comprising: rotating said first and second detectors and said source in a fixed relationship to each other by at least 360 degrees about said axis of rotation.

* * * * *